US005777215A

United States Patent [19]
Calatzis et al.

[11] Patent Number: 5,777,215
[45] Date of Patent: Jul. 7, 1998

[54] APPARATUS FOR MEASURING THE COAGULATION CHARACTERISTICS OF TEST LIQUIDS

[76] Inventors: Alexander Calatzis; Andreas Calatzis, both of Donnersbergerstrasse 42, 80634 München; Pablo Fritzsche, Adalbertsrasse 55, 80799 München, all of Germany

[21] Appl. No.: 669,465

[22] PCT Filed: Oct. 13, 1995

[86] PCT No.: PCT/EP95/04041

§ 371 Date: Sep. 12, 1996

§ 102(e) Date: Sep. 12, 1996

[87] PCT Pub. No.: WO96/12954

PCT Pub. Date: May 2, 1996

[30] Foreign Application Priority Data

Oct. 19, 1994 [DE] Germany .................. 44 37 475.
Apr. 4, 1995 [DE] Germany .................. 295 05 764.5

[51] Int. Cl.⁶ .................................................. G01N 33/49
[52] U.S. Cl. .......................... 73/64.41; 356/39; 422/73; 436/69
[58] Field of Search ................ 73/64.41, 64.42, 73/64.43, 64.53; 356/39; 422/73, 102; 436/69

[56] References Cited

U.S. PATENT DOCUMENTS

| 3,053,078 | 9/1962 | Jewett | 73/64.41 |
| 3,714,815 | 2/1973 | Hartert | 73/64.41 |

FOREIGN PATENT DOCUMENTS

| 404456 | 12/1990 | European Pat. Off. | |
| 2389137 | 4/1978 | France | |
| 845720 | 8/1952 | Germany | |
| 7616452 | 10/1970 | Germany | |
| 2740932 | 11/1978 | Germany | 73/64.41 |
| 3738901 | 5/1989 | Germany | 73/64.41 |
| 1353481 | 5/1974 | United Kingdom | 73/64.41 |

OTHER PUBLICATIONS

Shoupu Chen, Nitish V. Thakor and James W. Wagner, *A Microprocessor–Based Two–Channel Thromboelastograph*, IEEE Transactions on Biomedical Engineering, vol. BME–33, No. 9, at 887–890 (Sep. 1986).

*Primary Examiner*—Hezron E. Williams
*Assistant Examiner*—Daniel S. Larkin
*Attorney, Agent, or Firm*—Quarles & Brady

[57] ABSTRACT

An apparatus for measuring the coagulation characteristics of test liquids, in particular of blood samples, is provided. The apparatus comprises a plate (2, 20) with a bearing (3, 23) arranged in the plate (2, 20) and having an axis of symmetry which is substantially perpendicular to the plane of the plate. A shaft (1, 24) has a longitudinal axis extending substantially perpendicular to the plane of the plate and is connected with the bearing (3, 23). The first end of the shaft is located on one side of the plate (2, 20) and the second end of the shaft is located on the opposite side of the plate (2, 20). The apparatus further comprises means for sensing the rotational movement of the shaft (1, 24). A stem (29) is provided at the second end of the shaft (1, 24). A cup (40) serves for receiving the liquid. The inner contour of the cup is larger than the outer contour of the stem (29). The cup receives at least part of the stem. Finally, means for rotating the cup and the stem relative to each other and a spring device (4, 26) at the shaft (1, 24) are provided.

17 Claims, 7 Drawing Sheets

APPARATUS FOR MEASURING THE COAGULATION CHARACTERISTICS OF TEST LIQUIDS

The invention relates to an apparatus for measuring the coagulation characteristics of test liquids.

An apparatus for measuring the coagulation characteristics of test liquids is disclosed in DE 845 720 and DE-U 76 16 452. In this apparatus a rod is freely suspended at a torsion wire and provided with a stem at its lower end, which stem is immerged into a cup receiving the test liquid for measuring the coagulation characteristics of the test liquid. Usually about 0.36 ml of a test liquid, for example blood, will be in the cup. During the measurement the cup is rotated leftwards and rightwards by 4.75° with a harmonic motion and a period of 10 sec. Conventionally the cup has a diameter of 8 mm and the stem has a diameter of 6 mm. The measurement is based on the fact that the rotation of the cup is not transmitted to the stem as long as there is no link between the stem and the cup. If such a link is formed, for example by networks of fibrin fibres and platelets, the stem more and more follows the rotation of the cup. The forming network tends to counteract a difference in relative angle of rotation between the stem and the cup. Thus, a torque is transmitted from the rotating cup to the stem, and this torque is the higher the more pronounced the network between stem and cup is. On the other hand, the torsion wire acts against an excursion of the stem from its rest position. Hence, a torque equilibrium between the restoring torque of the torsion wire and the torque acting onto the stem is obtained, whereby inertial forces as well as viscous forces can be neglected, because the movements are very slow. The amplitude of the stem movement therefore represents a measure for the strength of the forming network or clot. The amplitude is exactly measured and plotted as a function of time. As outlined above, in the prior art apparatus the stem is freely suspended at the torsion wire through the corresponding rod, whereby the torsion wire exerts the above-mentioned restoring torque. This results in a high sensibility for vibration and translation movements of the measuring device, which distorts the measurements. One has tried to counteract these distorsions by providing the rod with laterally projecting paddles which are lowered into an oil-filled chambered trough. As explained in DE-U-76 16 452, in spite of the provision of the mentioned oil troughs and paddles, the sensitivity to disturbing influences is so high that an optical detection of the angle of rotation of the stem by means of known detection devices is disturbed. The known application describes an expensive inductive differential transformer angle sensor which is made to reduce signal disturbances resulting from movements of the stem which are not caused by the rotation thereof. The known devices consist of a large number of individually manufactured parts, which is expensive, and are again sensitive to shocks, because the respective measuring system is freely suspended. Furthermore, the known devices require an involved operation, because the chambers containing the oil must be filled and the systems must be exactly balanced. The transport of such an apparatus is extremely tedious, in particular because the oil containing chambers must be previously drained and again filled before further operation.

Further devices for measuring coagulation characteristics of blood samples are disclosed in GB 1 353 481 (FIG. 2).

It is the object of the invention to improve an apparatus of the initially defined kind so that it is more stable, less sensitive and easier to manufacture.

According to the invention a mechanical support system is provided which limits the decrease of freedom of the stem to the rotation around the normal or vertical axis.

The inventive apparatus guarantees a nearly frictionless function of the mechanical support system, preferably in form of a ball bearing. Hence, this apparatus allows an exact and correct movement of the stem even at a moment where the blood clot transmits an extremely small force to the stem. This is extremely important, because an important parameter of such devices, in particular in thrombelastographical applications, is the reaction time, i.e. the time from the start of the measurement to the moment where the stem performs about 1/100 of the cup movement of 4.75°, corresponding to less than 3 arc minutes. The invention ensures an exact measurement of the stem movement even at very small angles or very small forces, resp. The structure of the apparatus itself, with respect to the support of the stem, is simple, inexpensive and insensitive to disturbances.

Further features and advantages will be evident from a description of embodiments with reference to the figures.

FIRST EMBODIMENT

Figure 1:
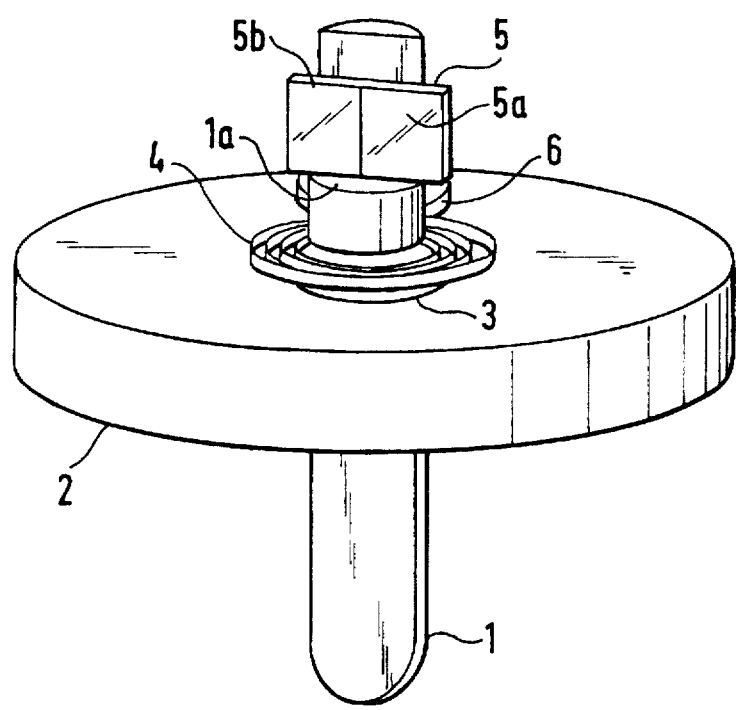
FIG. 1 is a perspective representation of the shaft and mechanical support means of a front of a first embodiment.
Figure 2:
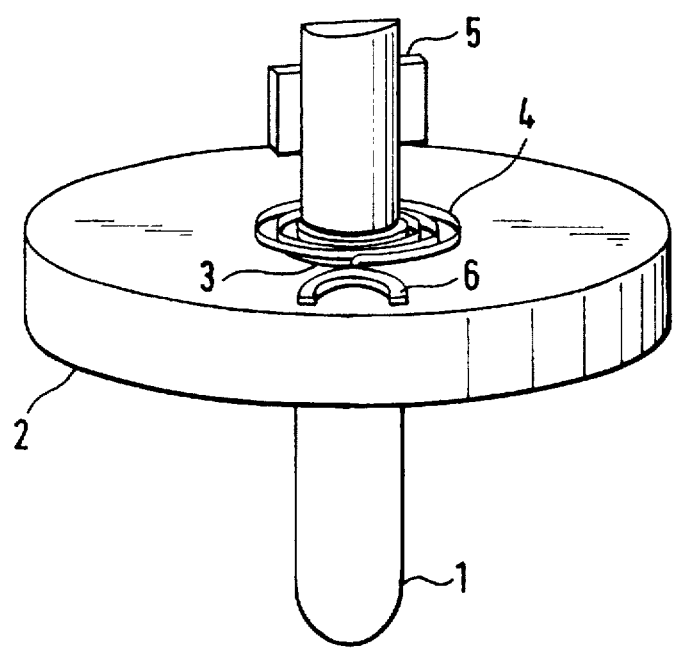
FIG. 2 is a back view corresponding to the representation of FIG. 1.
Figure 3:
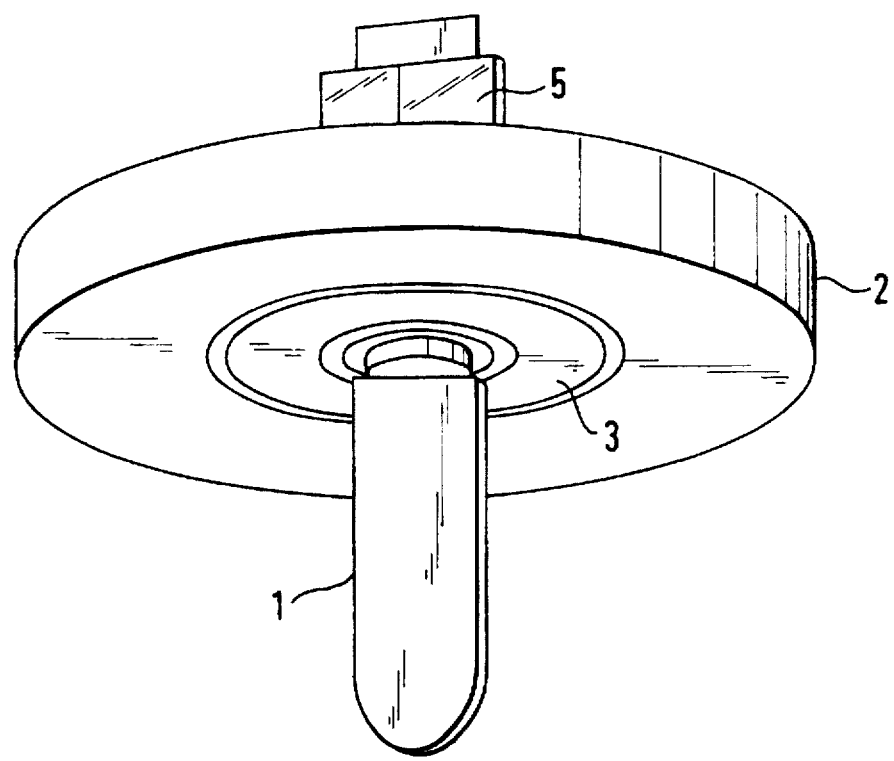
FIG. 3 is a representation corresponding to FIG. 1, seen from below.

The inventive apparatus is based on a sensor mechanism with mechanical support means and guided shaft according to FIGS. 1–3.

FIGS. 1–3 show the mechanical support device 3 supporting the shaft 1, as used in the inventive apparatus. A plastic stem cooperating with the blood for measurement can be appended to the lower end of the shaft 1. According to FIGS. 1–3 the shaft 1 is rotatably supported by the mechanical support device 3. Preferably, this support device is a roller bearing. This bearing is supposed to function as frictionless as possible. Particularly suitable is a ball bearing, for example a deep groove ball bearing of small diameter, for example 3 mm. Connected with the shaft 1 is the (not shown) stem appended to the lower part of the shaft, an angle detection device, for example a mirror 5 which is arranged at the upper end of the shaft 1 in a preferred embodiment according to FIGS. 1–3, a device for generating a restoring torque, preferably a spiral spring 4, and the rotating portion of the ball bearing. During the measurement, these components rotate together with the shaft and have an extremely small combined mass with the shaft, preferably less than one gram, to enable a rotation which is as frictionless as possible.

The ball bearing is inserted in a disk or plate 2. If a spiral spring 4 for generating a restoring torque acting onto the shaft 1 is present, one end of the spiral spring is fixed to the upper half of the shaft 1, as shown in FIG. 2, whereas the other end of the spiral spring 4 is fixed to the plate or disk 2.

Preferably, the spiral spring 4 is positioned in a plane above the ball bearing 3 and parallel thereto. The plate or disk 2 has fastening means 6, e.g. formed as a fixing cam or pin, for receiving the one end of the spiral spring 4. The shaft 1 has for example a slit for receiving the other end of the spiral spring 4.

The insertion of the ball bearing will be apparent from FIG. 3, whereas FIGS. 1 and 2 show the use of a spiral spring 4 exerting a restoring torque onto the shaft 1.

The mirror 5 is inserted into the shaft 1 so as to provide an information about the actual rotation of the shaft 1 using a detector beam. For this purpose a portion of the shaft 1 is milled away at the upper end of the shaft 1, as shown in FIG. 1. The shaft 1 receives the mirror 5 using the shoulder 1a formed thereby as a lower support therefor, as shown in FIG. 1.

In comparison with the rods used in the prior art, the shaft is relatively short, consists of light-weight material such as aluminum or ceramic or the like. Preferably, the shaft 1 is about midway along its length supported by the ball bearing 3.

In order to reduce the mass of the above-described rotating system as far as possible the angle of rotation of the shaft is detected through the mirror 5, preferably a small plane mirror. Preferably, the detection is performed using a collimated light beam, ideally a line-shaped light beam, a plane or concave mirror 5, and CCD-line sensor.

According to a further embodiment of the invention, a non-collimated light source, e.g. a diode, is used as beam generator and the mirror 5 is a plane mirror which is partly laminated with an opaque film 5a. The edge between the reflecting surface 5b and the non-reflecting surface 5a is imaged at the CCD-line sensor in an extremely exact and noise-free manner and the corresponding angle is calculated after detection by the CCD-line sensor, preferably using corresponding software.

The unit shown in FIGS. 1 to 3 has an extremely simple structure, requires few parts and allows the use of standard components, i.e. ball bearings and simple individual components such as a spiral spring, rectangular mirror, etc. This reduces the cost and considerably improves the reliability of the entire system.

Figure 4:
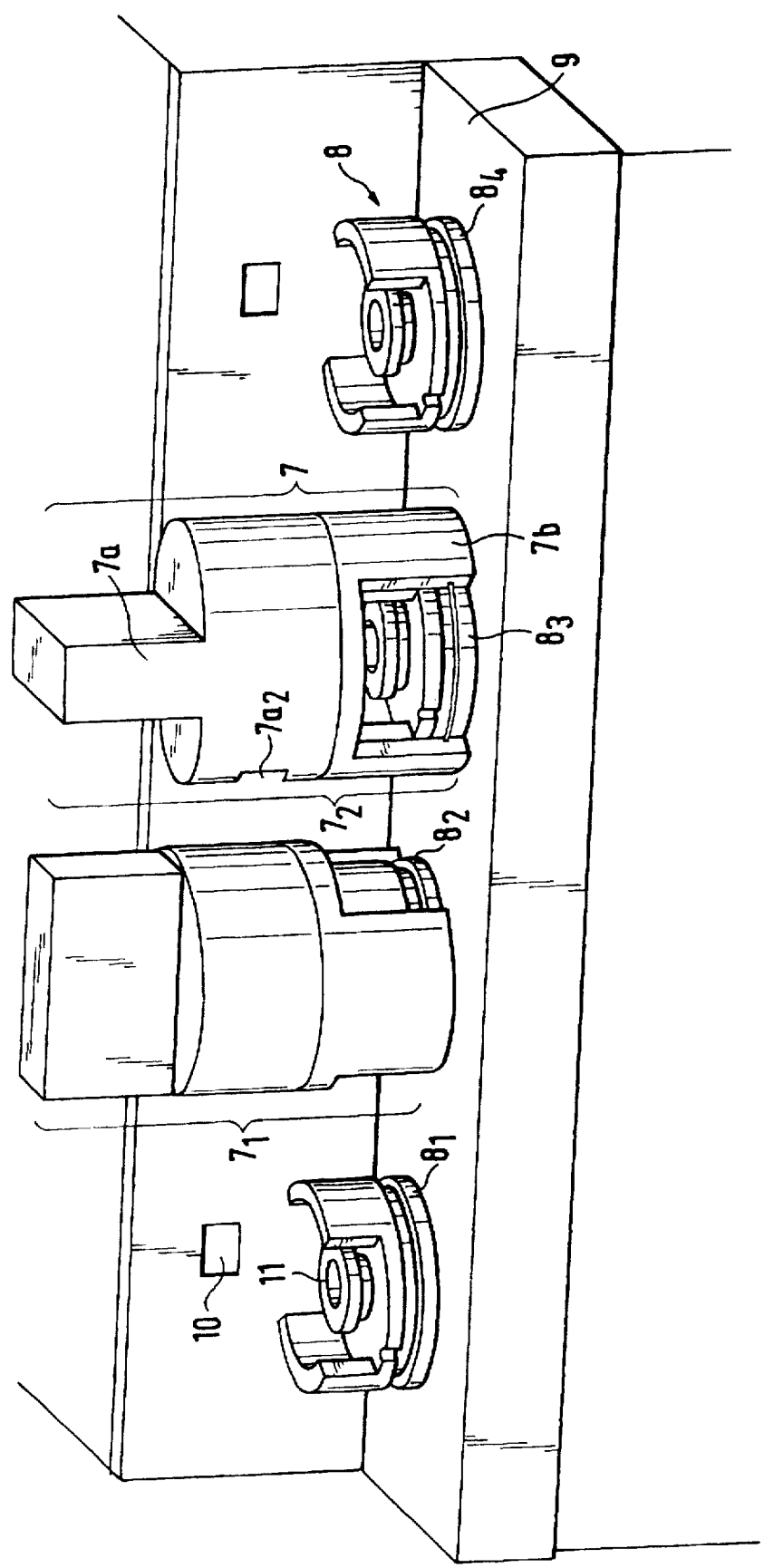
FIG. 4 is a perspective view of a portion of an inventive apparatus according to the first embodiment.

FIG. 4 is a perspective view of a preferred embodiment of the inventive apparatus.

A measuring unit of the inventive apparatus consists of a removable unit defined as a measuring cylinder 7 and a counterpiece 8 which is fixedly attached to the inventive apparatus.

Preferably, the inventive apparatus comprises four measuring units. Two complete measuring units are shown in FIG. 4 and referred to as $7_1$, $8_2$ and $7_2$, $8_3$, resp. The measuring cylinders 7 comprise the measuring mechanism shown in FIGS. 1 to 3 and can be put on the counterpieces 8 and rotated with respect thereto into a loading position and a testing position, as described below. According to a preferred embodiment, the counterpieces 8 cooperate with the measuring cylinders 7 to form a locking device in the form of a bayonet locking.

The base 9 is represented by a block which preferably consists of aluminum and which is heated to 36.5° by means of a thermostatic control.

Each counterpiece 8 has the cup receiver 11 in its center. The cup receiving the liquid to be tested, preferably blood, is placed into the cup receiver 11. In a conventional manner the cup receiver 11 together with the cups are rotated rightwards and leftwards by 4.75° in a harmonic movement. The cup receivers are in connection with the base 9 and passively heated thereby.

Preferably, the cups and test liquids are placed into the cup receivers in an open state as shown in FIG. 4 (counterpieces $8_1$ and $8_4$).

For exchanging the stem which is not shown in FIGS. 1 to 4, the measuring cylinder referenced by 7 is removed. To start the measurement, the measuring cylinder 7 is placed onto the counterpiece 8, whereby the stem immerges into the test liquid within the cup.

In the perspective view of FIG. 4, the measuring cylinder $7_2$ is shown in loading position, i.e. the measuring cylinder $7_2$ is rotated with respect to the counterpiece $8_3$ so that the sample may be visually controlled, as well as to cover the sample with a drop of oil in order to avoid drying out of the sample during the measurement.

The measuring cylinder 7 can be rotated with respect to the counterpiece 8 from the loading position so that the window $7a_2$ formed at the measurement cylinder directly opposes a window 10 in the rear wall of the housing. This is the test position according to counterpiece $8_2$ and measuring cylinder $7_1$. In this position a light beam or the like can pass from a beam generator arranged behind the window 10 to the mirror at the shaft within the measuring cylinder 7 and back into the interior of the housing. The CCD-line sensor for sensing the light beam reflected by the mirror is arranged in the interior of the housing.

An important advantage of the inventive apparatus results from the fact that all measuring cylinders 7 and cup receivers 11 are disposed on a commonly heated base 9 and thus passively heated.

An important advantage of the inventive apparatus also results from the fact that, by arranging the components shown in FIGS. 1 to 3 within the measuring cylinder 7, the shaft 1 together with the stem can manually be removed from the cup in an easy manner and an expensive mechanism for raising/lowering the measuring mechanism can be omitted.

The above-described sensing system comprising mirror 5 and corresponding light beams can be replaced by other sensing systems.

Figure 5:
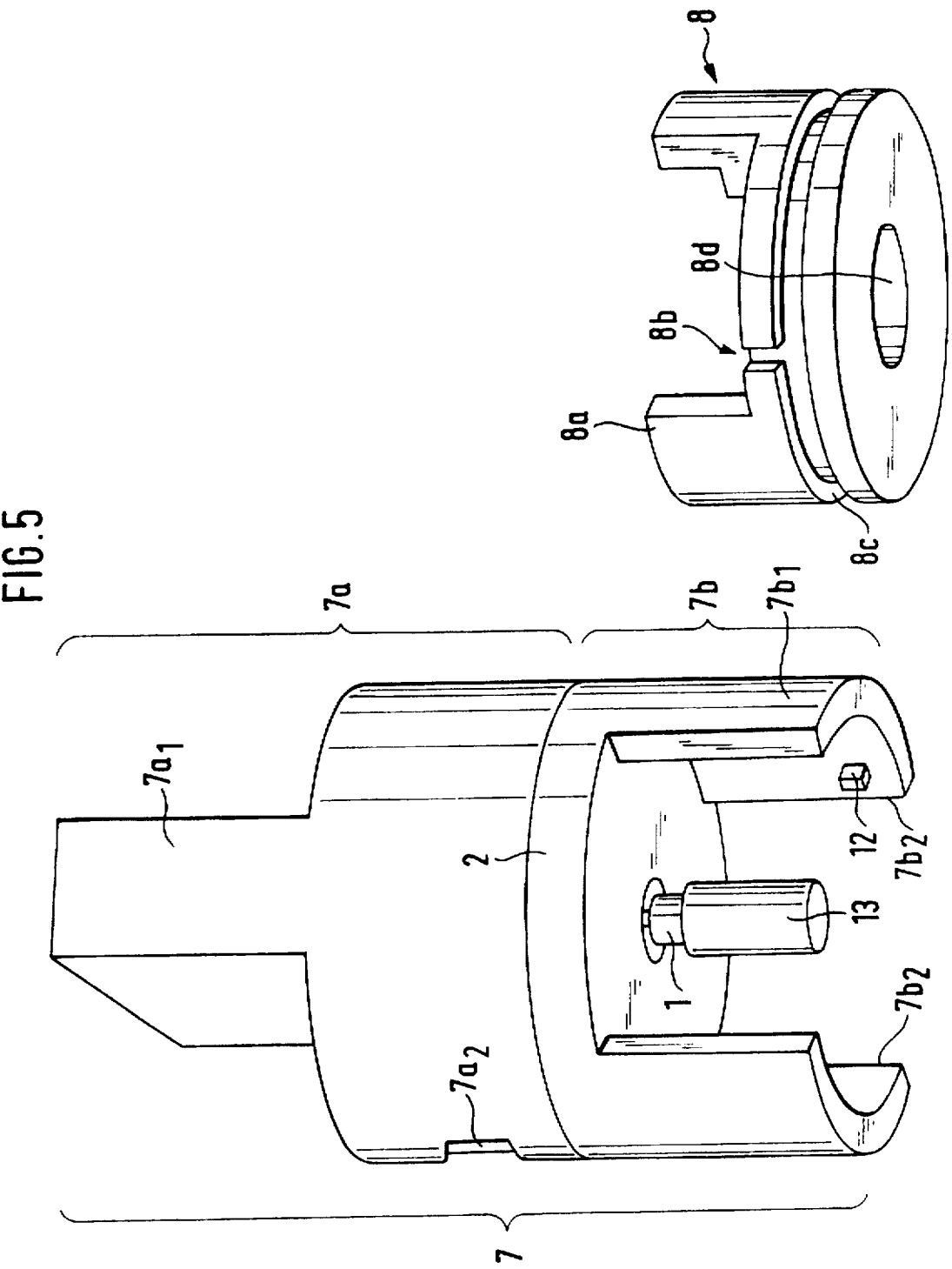
FIG. 5 is a perspective partial representation of the measuring station of the first embodiment.

FIG. 5 shows details of the measuring cylinder 7 and of the counterpiece 8.

Each unit 7 referred to as measuring cylinder consists of cylindrical parts 7a and 7b. The upper cylinder 7a has a handle $7a_1$ at its top and is preferably made of plastic. The cylinder 7a has a hollow interior and a lateral window $7a_2$ which is aligned opposite to window 10 (FIG. 4) in the test position.

The lower cylinder 7b has two lateral part-circular walls $7b_1$ and two corresponding apertures $7b_2$. Above the part-circular walls $7b_1$, the cylinder 7b has the disk 2 with the ball bearing (not shown in FIG. 5) and the supported shaft 1 being placed therein according to FIGS. 1 to 3. The upper part of the shaft 1 shown in FIGS. 1 to 3 with the spiral spring 4 and the mirror 5 projects into the upper cylinder 7a above the disk 2. The shaft 1 with the stem 13 appended to its lower end projects between the part-circular walls $7b_1$. The stem is made of plastic or the like and inserted into the cup in operation. Preferably, the lower cylinder 7b is made of aluminum, whereby it receives the heat from the thermostatically controlled base 9 according to FIG. 4 and is passively heated.

The counterpiece 8 shown in FIG. 5 is likewise cylindrical and has an outer diameter corresponding to the inner diameter of the measuring cylinder 7 so that the measuring cylinder 7 may be slipped onto the counterpiece 8. Thereby the rod 12 attached to the part-circular walls $7b_1$ of the measuring cylinder 7 is introduced into the annular groove 8c of the counterpiece 8 through the slit 8b. The measuring cylinder 7 may be rotated with respect to the counterpiece 8 when slipped on. A position whereby the part-circular walls 8a formed at the counterpiece 8 are placed behind the part-circular walls $7b_1$ formed at the measuring cylinder 7 and are therefore covered thereby, is a loading position. In this position, the sample can be freely inspected. By a rotation about 90°, the measuring cylinder is brought into the testing position whereby the lock between the measuring cylinder and the counterpiece is caught in an exact position. In this position, the part-circular walls $7b_1$ and 8a alternate, i.e. they are placed side by side and substantially enclose the air volume between the measuring cylinder and the counterpiece so as to prevent the cooling of the test liquid during the measurement by convection or air draft. A cool-down of the test liquid during the measurement would slow down the processes occurring during coagulation of blood and would distort the result of the measurement. The counterpiece 8 is preferably made of plastic. The center of the counterpiece 8 is provided with a circular hole 8d for receiving the cup receiver 11 shown in FIG. 4.

SECOND EMBODIMENT

Figure 6:
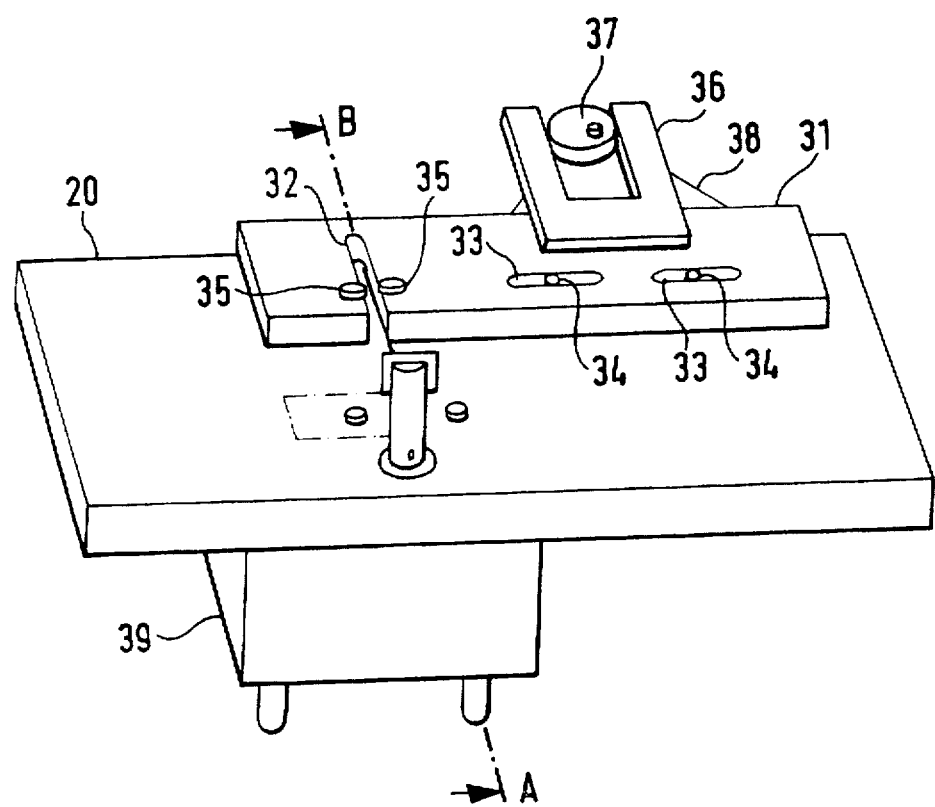
FIG. 6 is a schematic perspective representation of a second embodiment.
Figure 7:
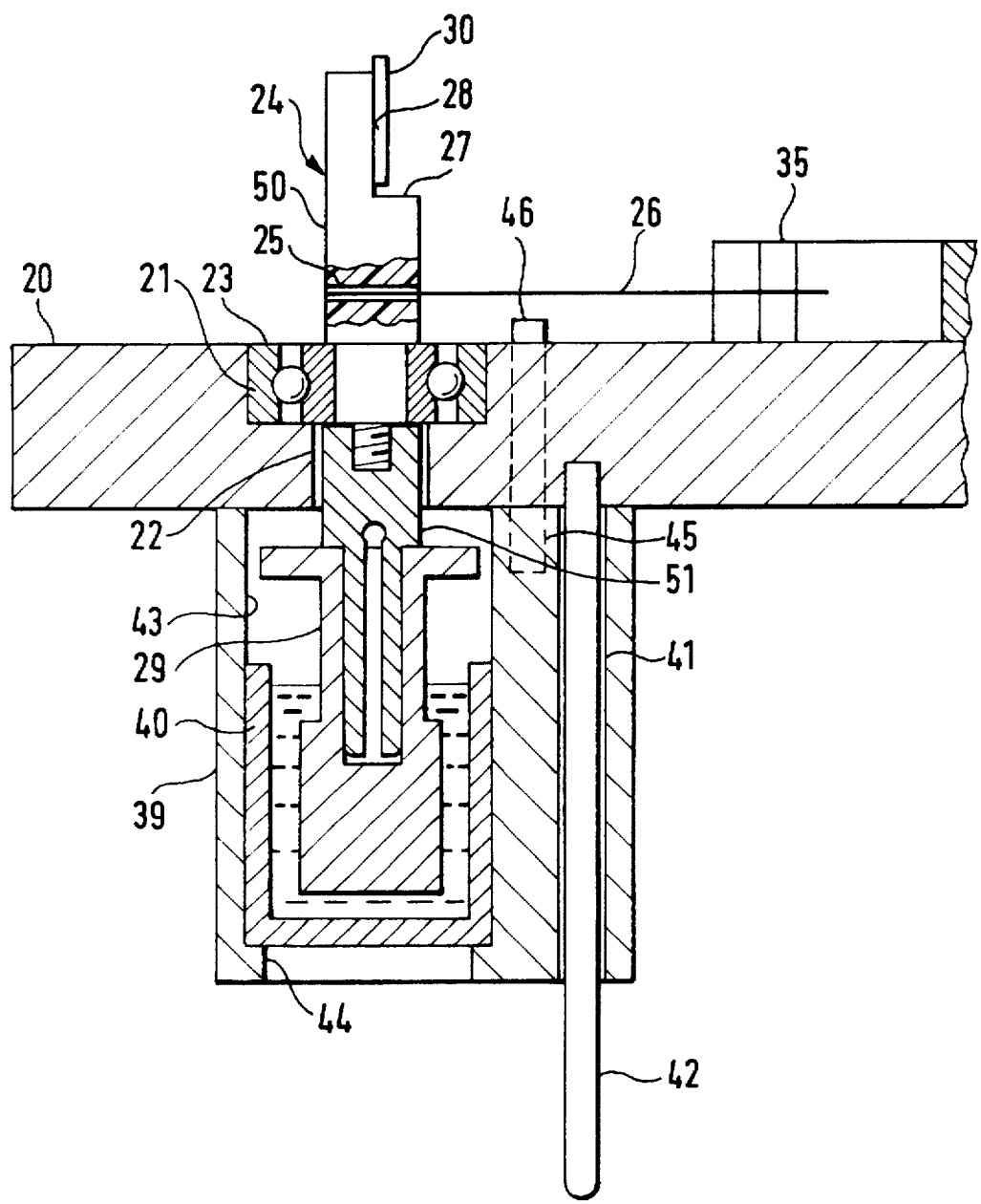
FIG. 7 shows a section along line A–B of FIG. 6.

A plate 20 is provided. As shown in FIGS. 6 and 7 the plate 20 has a first bore 21 extending perpendicular to the plane of the plate and having a first diameter. The first bore 21 is followed by a coaxial second bore 22 having a second diameter which is smaller than the first diameter. The length of the bores 21, 22 corresponds to the dimension of the plate 20 in a direction perpendicular to the plane of the plate. A ball bearing 23 is coaxially disposed within the first bore 21. The outer diameter of the ball bearing corresponds to about the first diameter and the inner diameter of the ball bearing is smaller than the second diameter.

A substantially cylindrical shaft 24 is coaxially connected with the inner ring of the ball bearing 23.

The shaft 24 has an upper first part 50 and a lower second part 51 screwed to the first part. The first part 50 comprises a first cylindrical portion having a diameter which is greater than the inner diameter of the ball bearing. The upper end of the first portion is provided with a shoulder 27 so as to form a plane 28 which is parallel to the longitudinal axis of the shaft 24. A mirror 30 is attached to the plane 28.

The lower end of the first portion is coaxially followed by a second portion having an outer diameter designed to snugly fit into the ball bearing 23. The length of the second portion corresponds to the axial dimension of the ball bearing 23. The second portion is coaxially followed by a third portion having an outer diameter which is smaller than that of the second portion. The third portion has an external screw thread. The second part 51 has a fourth portion having a diameter which is greater than the inner diameter of the ball bearing 23 and smaller than the second diameter of the second bore 22. One end of the fourth portion is provided with a coaxial cylinder bore having an internal screw thread matching the external screw thread of the third portion of the first part 50. The fourth portion of the second part is coaxially followed by a fifth portion having a smaller diameter than the fourth portion. The fifth portion has an axially extending slot. The slot end adjacent to the fourth portion comprises a through-bore extending perpendicular to the axial direction of the fifth portion.

The second portion of the first part 50 is arranged within the ball bearing 23. The second part 51 is screwed onto the first part so that both parts 50, 51 are connected with the inner ring of the ball bearing 23.

A third bore 25 extending perpendicular to the longitudinal axis of the shaft 24 is provided in the first part 50 of the shaft 24 spaced from the side of the plate 20 associated to the first bore 21 in direction to the first end of the first part 50 of the shaft 24. Preferably, the third bore 25 is a through-bore. A straight spring wire 26 is arranged parallel to the plane of the plate and has one end thereof mounted within the third bore 25. Preferably, the spring wire 26 is glued into the third bore.

A substantially cylindrical stem 29 has one end with a coaxial bore having a diameter which is slightly smaller than the diameter of the fifth portion of the second part 51. The stem is slipped onto the fifth portion and attached to the shaft 24 by the resilient force of the fifth portion.

A support plate 31 is provided at the side of the plate 20 corresponding to the first part 50 of the shaft 24 (FIG. 6). Two spaced elongate holes 33 are provided in the support plate 31. The longitudinal axes of the elongate holes 33 are parallel. A corresponding guide pin 34 fixed in the plate 20 is arranged in each elongate hole 33 in a direction perpendicular to the plane of the plate so that the support plate 31 may slide on the plate 20 only in direction of the elongate holes 33. A slot 32 is provided in the support plate 31 perpendicular to the longitudinal axes of the elongate holes 33. The dimension of the slit in direction of the longitudinal axis of the elongate holes 33 is greater than the diameter of the spring wire 26. Respective guide drums 35 are arranged on both sides of the slot 32 in direction of the longitudinal axes of the elongate holes 33. The longitudinal axes of the guide drums are parallel with the longitudinal axes of the shaft 24 and the guide drums are facing each other in direction of the longitudinal axes of the elongate holes 33 so that the minimum distance therebetween is greater than the diameter of the spring wire 26 and smaller than the dimension of the slit 32 in longitudinal direction of the elongate holes 33. The support plate 31 with the slot 32 is provided on the plate 20 so that an end of the spring wire 26 facing away from the shaft 24 is disposed between the guide drums 35.

Preferably, the play between the spring wire 26 and the guide drums is about 0.3 mm and the diameter of the spring wire 26 is between 0.1 mm and 0.2 mm.

A U-shaped plate 36 is mounted on the support plate 31 so as to be parallel thereto. The two legs of the U-shaped plate 36 extend perpendicular to the longitudinal axis of the elongate holes 33 and project beyond the support plate. An eccentric shaft 37 having a longitudinal axis extending parallel to the longitudinal axis of the shaft 24 is disposed between the two legs. The shaft 37 is eccentrically connected with a drive shaft of a motor 38.

A box-shaped cup receiver 39 comprises a first cup bore 43 and a following coaxial second cup bore 44. The longitudinal axes of both cup bores are perpendicular to a first side of the box. The cup bores 43, 44 extend across the entire length of the box in longitudinal direction of the cup bores 43, 44. A cup 40 is provided within the first cup bore 43. The diameter of the first cup bore 43 corresponds to about the outer diameter of the cup 40. The diameter of the second cup bore is smaller than the diameter of the first cup bore. Two spaced fourth through-bores 41 are provided parallel to the cup bores 43, 44.

Two guide rods 42 are provided on the side of the plate 20 corresponding to the second part 51 of the shaft 24. The guide rods are spaced by a distance corresponding to the spacing of the fourth bores 41 and have a longitudinal axis arranged parallel to the longitudinal axis of the shaft 24. Each guide rod 42 is associated to a corresponding one of the fourth bores 41. The diameter of the fourth bores is adapted to allow a sliding movement of the cup receiver 39 on the guide rods 42. The fourth bores 41 and the first cup bore 43 as well as the guide rods 42 and the shaft 24 carrying the stem 29 are arranged so that the cup 40 at least partially receives the stem 29, if the cup receiver 39 is slipped on the guide rods 42 and its first side surface contacts the side of the plate 20 facing the stem 29. Two spaced metal cylinders are provided in the cup receiver 39. Respective magnets 46 are provided at corresponding locations on the side of the plate 20 facing the first part 50 of the shaft 24. The cup receiver 39 is magnetically attached to the plate 20 by means of the magnets 46 and the metal cylinders 45. The metal cylinders 45 can also be magnetic, in which event, the magnets 46 may optionally be substituted with non-magnetic metal members.

Preferably, the plate 20 and the cup receiver 39 are made of aluminum, the first part 50 of the shaft is made of plastic and the second part 51 of the shaft is made of stainless steel. Preferably, the plate 20 is electrically heated and held on a constant temperature of about 37° C. In this manner the test liquid, preferably blood, provided within the cup is indirectly heated through the cup receiver 39.

In operation, the cup receiver 39 containing the blood-filled cup 40 is magnetically attached to the plate 20. The stem 29 is in contact with the blood. The eccentric shaft 37 is rotated by the motor 38. This rotational motion of the eccentric shaft 37 is transformed into a periodical movement of the support plate 31 in longitudinal direction of the elongate holes 33 using the U-shaped plate 36. Further, this periodical movement of the support plate 31 is transformed into a periodical rotational movement of the shaft 24 through the guide drums 35 and the spring wire 36. Unless there is a force acting on the stem 29 against the direction of rotation of the shaft 24 the shaft 24 performs the full periodical rotational movement of 4.75°. The angle of rotation of the shaft 24 is measured using the mirror 30 according to one of the manners described in connection with the first embodiment.

Since the spacing of the guide drums 35 in the longitudinal direction of the elongate holes 33 is greater than the diameter of the spring wire 26 there is ideally a punctual contact between the guide drum 35 and no tensile forces are therefore exerted onto the spring wire 26. If a connection forms between the stem 29 and the cup 40, e.g. by means of fibrin fibres and platelets, a torque acts against the rotational movement of the stem 29. This torque causes the spring wire 26 to bend, whereby the shaft 24 is no longer completely rotated. Rather, an instantaneous angle of rotation of the shaft 24 and therefore its amplitude with respect to the periodical rotational movement is determined by the actual equilibrium between the torque caused by the clot and the torque effected by the bending of the spring wire. Thus, the amplitude of the rotational movement of the shaft 24 with the stem 29 represents a measure for the strength of the forming network or clot.

Figure 8:
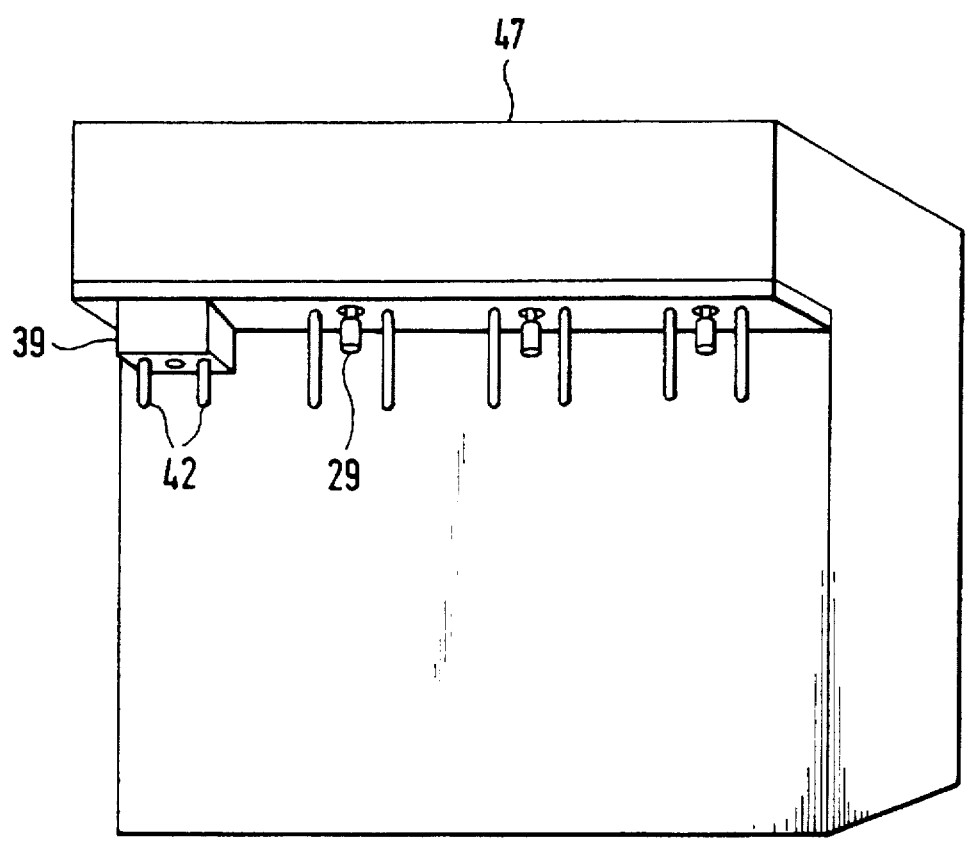
FIG. 8 is a perspective view of a measuring station according to the second embodiment.

The assembly of a measuring station is shown in FIG. 8. Four spaced shafts 24 are provided. The support plate has a corresponding slot 32 with respective two guide drums 35 for each spring wire 26. The entire drive of the support plate 31 and the complete optical measuring system for measuring the excursion of the respective shaft 24 is located in a closed housing 47. Only the cup 40 containing the test liquid and the cup receiver, resp., are replaced for measurement.

In this embodiment the ball bearing 23 can be measured in idling state, because the shaft 24 is driven and simultaneously the excursion thereof is measured. Erroneous measurements caused by a defect ball bearing can therefore be better excluded.

Furthermore, in this embodiment the entire optical system as shown in FIG. 8 can be enclosed. Only the cup receiver is exchanged for measurement. Thus, the entire system is less sensitive to disturbations.

Since in this embodiment the ball bearing is always rotated, a more exact measurement is possible, because there is, in contrast to the first embodiment, no static moment of the ball bearing which must be overcome.

In the description blood was mentioned as liquid to be measured. However, any other test liquid can be measured using the described embodiments.

We claim:

1. Apparatus for measuring the coagulation characteristics of test liquids, in particular of blood samples, said apparatus comprising a plate means defining a plane, bearing means having an axis of symmetry, said bearing means being disposed in said plate means with said axis of symmetry extending substantially perpendicular to said plane, shaft means having a longitudinal axis, a first end and a second end, said shaft means being rotatably supported in said bearing means to extend substantially perpendicular to said plane with said first end being disposed on one side of said plate and said second end on the other side of said plate, means for sensing a rotational movement of said shaft means, a stem being provided at said second end and having an outer contour, a cup for receiving said test liquid, said cup having an inner contour which is larger than said outer contour of said stem and receiving at least part of said stem, means for rotating said cup and said stem relative to each other, and spring means arranged at said shaft.

2. The apparatus of claim 1, said rotating means being arranged to drive said shaft means.

3. The apparatus of claim 1, comprising a cup receiver for receiving said cup, said cup receiver having a first plane side and two spaced through-bores having a first diameter and extending substantially perpendicular to said first side, two guide rods each having a respective one end connected to said plate and a respective other end extending parallel to said shaft means, said guide rods being spaced corresponding to said spacing of said through-bores and extending substantially perpendicular to said plane, said guide rods being dimensioned to just fit into said through-bores so as to allow a sliding movement of said cup receiver on said guide rods.

4. The apparatus of claim 3, comprising a first member provided in said cup receiver close to said first side thereof, and a second member at or within said plate, said first and second members exerting an attractive force onto each other.

5. The apparatus of claim 4, wherein one of said members is a magnet.

6. The apparatus of claim 1, wherein said spring means comprises a first end and a second end, said first end being connected to said shaft and said spring means extending substantially parallel to said plate.

7. The apparatus of claim 6, comprising two guide drums projecting in a substantially perpendicular direction to said plane, said second end of said spring means being arranged between said guide drums with a predetermined play therebetween.

8. The apparatus of claim 7, comprising a support plate having two spaced elongate holes with parallel longitudinal axes, a respective guide pin arranged in each of said elongate holes and connected to said plate for providing a defined sliding movement of said support plate in the longitudinal direction of said elongate holes within a predetermined region.

9. The apparatus of claim 8, comprising means for moving said pins by means of said support plate and a receiver mounted at said support plate and having two spaced parallel legs, an eccenter being disposed between said legs.

10. The apparatus of claim 1, wherein said rotating means drives said cup.

11. The apparatus of claim 1, wherein said spring means comprises a leaf spring or a spring wire.

12. The apparatus of claim 10, wherein said spring means comprises a spiral spring.

13. The apparatus of claim 10, said spiral spring comprising one end fixed to said plate means and another end fixed to said shaft means.

14. The apparatus of claim 1, said bearing means comprising a ball bearing.

15. The apparatus of claim 1, wherein at least part of said shaft means is made of aluminum.

16. The apparatus of claim 1, comprising a slit provided at said first end of said shaft means for receiving a mirror or the like.

17. The apparatus of claim 16, wherein said mirror is a plane mirror or a concave mirror.

* * * * *